(12) United States Patent
Farra

(10) Patent No.: US 10,780,216 B2
(45) Date of Patent: *Sep. 22, 2020

(54) IMPLANTABLE MEDICAL DEVICE FOR MINIMALLY-INVASIVE INSERTION

(71) Applicant: Microchips Biotech, Inc., Lexington, MA (US)

(72) Inventor: Robert Farra, Acton, MA (US)

(73) Assignee: MICROCHIPS BIOTECH, INC., Lexington, MA (US)

(*) Notice: Subject to any disclaimer, the term of this patent is extended or adjusted under 35 U.S.C. 154(b) by 149 days.

This patent is subject to a terminal disclaimer.

(21) Appl. No.: 15/644,082

(22) Filed: Jul. 7, 2017

(65) Prior Publication Data

US 2017/0304533 A1    Oct. 26, 2017

Related U.S. Application Data

(63) Continuation of application No. 14/192,605, filed on Feb. 27, 2014, now Pat. No. 9,700,668.

(Continued)

(51) Int. Cl.
   *A61M 5/142*     (2006.01)
   *A61K 9/00*      (2006.01)
   *A61M 31/00*     (2006.01)

(52) U.S. Cl.
   CPC ....... *A61M 5/14276* (2013.01); *A61K 9/0097* (2013.01); *A61M 31/002* (2013.01);
   (Continued)

(58) Field of Classification Search
   CPC .. A61M 2205/3507; A61M 2205/0244; A61M 2205/04; A61M 5/14276;
   (Continued)

(56) References Cited

U.S. PATENT DOCUMENTS 4,544,577 A * 10/1985 May ...................... C04B 41/009
                                                    427/205
5,782,891 A    7/1998 Hassler et al.
(Continued)

FOREIGN PATENT DOCUMENTS

EP        1540727 B1    10/2010
WO    2012/027137 A1     3/2012

OTHER PUBLICATIONS

Antlia SA. Ithetis Implantable Drug Delivery Device. Lausanne: Antlia, 2011. Ithetis Implantable Drug Delivery Device. May 5, 2012. Web. Mar. 11, 2015. <https://web.archive.Org/web/20120505100735/http://www.ithetis.com/product/overview/>. (Year: 2011).*
(Continued)

*Primary Examiner* — Bhisma Mehta
*Assistant Examiner* — James D Ponton
(74) *Attorney, Agent, or Firm* — Eversheds Sutherland (US) LLP

(57) ABSTRACT

In one aspect, containment devices are provided that include a microchip element having one or more containment reservoirs that are configured to be electrically activated to open; an electronic printed circuit board (PCB) or a silicon substrate positioned adjacent to the microchip element; one or more electronic components associated with the microchip element or the PCB/silicon substrate; and a first inductive coupling device associated with the microchip element or the PCB/silicon substrate, wherein the first inductive coupling device is in operable communication with the one or more electronic components. In another aspect, implantable drug delivery devices are provided that include a body housing at least one drug payload for actively controlled release, wherein the ratio of the volume of the at least one drug payload to the total volume of the implantable drug delivery device is from about 75 μL/cc to about 150 μL/cc.

13 Claims, 8 Drawing Sheets

Related U.S. Application Data

(60) Provisional application No. 61/770,486, filed on Feb. 28, 2013.

(52) U.S. Cl.
CPC . *A61M 2205/0244* (2013.01); *A61M 2205/04* (2013.01); *A61M 2205/3515* (2013.01); *Y10T 29/49128* (2015.01)

(58) Field of Classification Search
CPC .. A61M 5/172; A61M 5/1723; A61M 31/002; A61M 2205/50; A61B 5/07; A61K 9/0097
See application file for complete search history.

(56) References Cited

U.S. PATENT DOCUMENTS

| | | | |
|---|---|---|---|
| 6,052,623 A | 4/2000 | Fenner et al. | |
| 6,123,861 A | 9/2000 | Santini, Jr. et al. | |
| 6,491,666 B1 | 12/2002 | Santini, Jr. et al. | |
| 6,527,762 B1 | 3/2003 | Santini, Jr. et al. | |
| 6,551,838 B2 | 4/2003 | Santini, Jr. et al. | |
| 6,773,429 B2 | 8/2004 | Sheppard, Jr. et al. | |
| 6,808,522 B2 | 10/2004 | Richards et al. | |
| 6,827,250 B2 | 12/2004 | Uhland et al. | |
| 6,875,208 B2 | 4/2005 | Santini, Jr. et al. | |
| 6,976,982 B2 | 12/2005 | Santini, Jr. et al. | |
| 7,070,590 B1 | 7/2006 | Santini, Jr. et al. | |
| 7,114,312 B2 | 10/2006 | Coppeta et al. | |
| 7,226,442 B2 | 6/2007 | Sheppard, Jr. et al. | |
| 7,354,597 B2 | 4/2008 | Johnson et al. | |
| 7,413,846 B2 | 8/2008 | Maloney et al. | |
| 7,488,316 B2 | 2/2009 | Prescott et al. | |
| 7,497,855 B2 | 3/2009 | Ausiello et al. | |
| 7,510,551 B2 | 3/2009 | Uhland et al. | |
| 7,534,241 B2 | 5/2009 | Coppeta et al. | |
| 7,537,590 B2 | 5/2009 | Santini, Jr. et al. | |
| 7,599,737 B2 | 10/2009 | Yomtov et al. | |
| 7,604,628 B2 | 10/2009 | Santini, Jr. et al. | |
| 7,608,919 B1 * | 10/2009 | Bernstein | H01L 23/60 257/685 |
| 7,621,905 B2 * | 11/2009 | Penner | A61K 9/0009 604/891.1 |
| 7,917,208 B2 | 3/2011 | Yomtov et al. | |
| 8,095,197 B2 | 1/2012 | Santini, Jr. et al. | |
| 8,191,756 B2 | 6/2012 | Coppeta et al. | |
| 8,604,810 B2 | 12/2013 | Sheppard, Jr. | |
| 8,649,840 B2 | 2/2014 | Sheppard, Jr. et al. | |
| 9,700,668 B2 * | 7/2017 | Farra | A61K 9/0097 |
| 2001/0044620 A1 | 11/2001 | Krulevitch et al. | |
| 2002/0072784 A1 * | 6/2002 | Sheppard, Jr. | A61B 5/14539 607/60 |
| 2002/0187260 A1 * | 12/2002 | Sheppard, Jr. | A61K 9/0009 427/248.1 |
| 2003/0034564 A1 | 2/2003 | Palanisamy et al. | |
| 2003/0080085 A1 | 5/2003 | Greenberg et al. | |
| 2004/0247671 A1 | 12/2004 | Prescott et al. | |
| 2005/0245799 A1 * | 11/2005 | Brauker | A61B 5/14532 600/347 |
| 2006/0076236 A1 | 4/2006 | Shah et al. | |
| 2007/0236859 A1 * | 10/2007 | Borland | C08G 59/621 361/272 |
| 2008/0191581 A9 * | 8/2008 | Penner | A61K 9/0097 310/311 |
| 2009/0222066 A1 * | 9/2009 | Chen | A61N 1/37229 607/61 |
| 2010/0022992 A1 | 1/2010 | Genosar et al. | |
| 2010/0119604 A1 | 5/2010 | Prescott et al. | |
| 2010/0149042 A1 | 6/2010 | Utsi et al. | |
| 2011/0237935 A1 | 9/2011 | Kalpin et al. | |
| 2012/0035528 A1 | 2/2012 | Coppeta et al. | |
| 2012/0130339 A1 | 5/2012 | Farra | |
| 2012/0209100 A1 | 8/2012 | De Beeck et al. | |
| 2013/0053671 A1 | 2/2013 | Farra | |
| 2013/0211219 A1 | 8/2013 | Coppeta et al. | |

OTHER PUBLICATIONS

Santini, Jr. et al, "Microchips as Controlled Drug-Delivery Devices", Angew Chem Int Ed Engl. Jul. 17, 2000; 39 (14):2396-2407.
Antlia SA. Ithetis Implantable Drug Delivery Device. Lausanne: Antlia, 2011.1thetis Implantable Drug Delivery Device. May 5, 2012. Web. Mar. 11, 2015. https://web.archive.org/web/20120505100735/http://www.ithetis.com/product!overview/22 .
LaMeres, "Characterization of a Printed Circuit Board Via", M.S Thesis, University of Colorado, Colorado Springs, CO, 2001.

* cited by examiner

IMPLANTABLE MEDICAL DEVICE FOR MINIMALLY-INVASIVE INSERTION

CROSS-REFERENCE TO RELATED APPLICATION

This application is a continuation of U.S. application Ser. No. 14/192,605, filed Feb. 27, 2014, which claims priority to and the benefit of U.S. Application No. 61/770,486, filed Feb. 28, 2013, all of which are incorporated herein by reference.

FIELD

The present disclosure relates generally to multi-reservoir containment devices, including but not limited to medical devices, such as implantable medical devices, having containment reservoirs for confining substance or subcomponents for controlled release or exposure thereof. In aspects, the present disclosure relates to improved designs of such devices for minimally invasive implantation and operation.

BACKGROUND

Implantable medical devices based on microchips that include reservoir arrays containing biosensors or drugs, for example, are known in the art. FIG. 1 shows a possible conventional approach for assembly of components in an implantable medical device 10, which includes a microchip assembly 12. The microchip assembly 12, which is also referred to as a microchip element, includes microreservoirs, each of which may contain a drug for controlled delivery in vivo or a sensor for controlled exposure in vivo. The microchip assembly 12 is attached to a feedthrough 16 that is welded to the housing 14. Such microchip assemblies or elements are described, for example, in U.S. Pat. No. 7,510,551 to Uhland et al. and U.S. Pat. No. 7,604,628 to Santini Jr. et al. The feedthrough 16 contains electrically conductive pins that are metallurgically brazed to metallized surfaces on and through an alumina disc. A typical pin count exceeds 100, and in more complex designs, can be over 400. The consequence of such designs is that each pin connection can be a leak point.

In addition, each feedthrough pin is electrically connected to an electronic component inside the housing. Some designs utilize a wire from the pin to the circuit, while the illustrated design attaches the feedthrough 16 directly to a conventional plastic circuit board 18. These electrical connections require testing to ensure continuity. As a result, the pin count impacts the cost of the feedthrough, and that cost increases as the number of feedthrough pins increases in the implantable device. Consequently, due to this complex design requirement, the resulting manufacturing, and the required acceptance tests, the feedthrough is an expensive component.

Moreover, conventional implantable device designs based on a feedthrough or header attached to housing components disadvantageously have an overall volume of the resulting device that is larger than desired, because several discrete components make up the assembly.

The devices shown in FIG. 1 contains control electronics, a power source, and wireless communication capabilities. The benefit of these internal functions is that the device can be programmed to automatically release discrete doses at specific time points, and the dosing schedule can be updated or modified wirelessly at any time. The patient therefore can automatically receive his or her medication without having to take any action. A disadvantage to this automatic drug delivery implant is that all of these functions require a finite volume. There is a clear desire, however, to reduce the volume of the device in order to i) reduce the incision required to implant the device under the skin, ii) increase the possible locations in the body that the device can be implanted, and iii) make the device less intrusive for the patient. In particular, it would be desirable to provide a smaller overall device volume without sacrificing functionality, simplicity, and/or hermeticity.

SUMMARY

Some or all of the above needs and/or problems may be addressed by certain embodiments of the disclosure. In one embodiment, a containment device is provided that includes an elongated microchip element comprising one or more containment reservoirs that are configured to be electrically activated to open. The containment device may also include an elongated electronic printed circuit board (PCB) comprising a biocompatible substrate. The elongated PCB also may include a first side on which one or more electronic components are fixed and an opposed second side on which the elongated microchip element is fixed in electrical connection to the one or more electronic components. Further, the containment device may include an elongated housing fixed to the elongated PCB. The elongated housing is configured to hermetically seal the one or more electronic components of the elongated PCB within the elongated housing.

Other embodiments, aspects, and features of the invention will become apparent to those skilled in the art from the following detailed description, the accompanying drawings, and the appended claims.

BRIEF DESCRIPTION OF THE DRAWINGS

Reference will now be made to the accompanying drawings, which are not necessarily drawn to scale.

DETAILED DESCRIPTION

Illustrative embodiments will now be described more fully hereinafter with reference to the accompanying drawings, in which some, but not all embodiments are shown. The representative embodiments described in the disclosure may be embodied in many different forms and should not be construed as limited to the embodiments set forth herein. Like numbers refer to like elements throughout.

The containment devices and assemblies described herein provide, among other advantages, significantly improved space efficiency of the assembled devices. In certain embodiments, the devices and methods advantageously eliminate the need for a costly and complex feedthrough, provide a thinner, sleek implant due to the elimination of the feedthrough, provide improved reliability by eliminating numerous feedthrough pins and electrical connections, provide improved reliability by reducing the number of hermetic interfaces, simplify tests to confirm functionality, and provide a simpler assembly. This can be particularly important in embodiments in which the containment device is an implantable medical device intended for long-term implantation in a human or animal subject via minimally-invasive insertion means, such as through a small incision, trocar, cannula, injector, or similar like medical instrument.

The present invention advantageously provides a drug delivery implant with a higher ratio of drug volume to total device volume than previously available for an actively controlled implant device. For example, a theoretical, perfect drug delivery device, with zero device volume could have a ratio of 1000 µL/cc. In practice, conventional drug delivery devices may range from less than 1 µL/cc to about 65 µL/cc. Advantageously, by providing the containment devices described herein and relocating power source and control functions to an external communicator as described herein, a drug delivery implant having a ratio of drug volume to total device volume from about 80 µL/cc to about 120 µL/cc, or higher, is readily achievable. In one embodiment, the implantable drug delivery device has a body housing a drug payload for actively controlled release, which device has a ratio of volume of the drug payload to total volume of the device from about 75 µL/cc to about 150 µL/cc. In one case, for example, the ratio is from about 85 µL/cc to about 120 µL/cc. In one embodiment, the body of the implantable drug delivery device includes a microchip element that has one or more containment reservoirs that are configured to be electrically activated to open; a PCB fixed to the microchip element; and a first inductive coupled device associated with the microchip element or the PCB, wherein the first inductive coupling device is in communication with the one or more electronic components. Nevertheless, essentially any ratio of drug volume to total device volume may be used with the devices and systems described herein.

Figure 1:
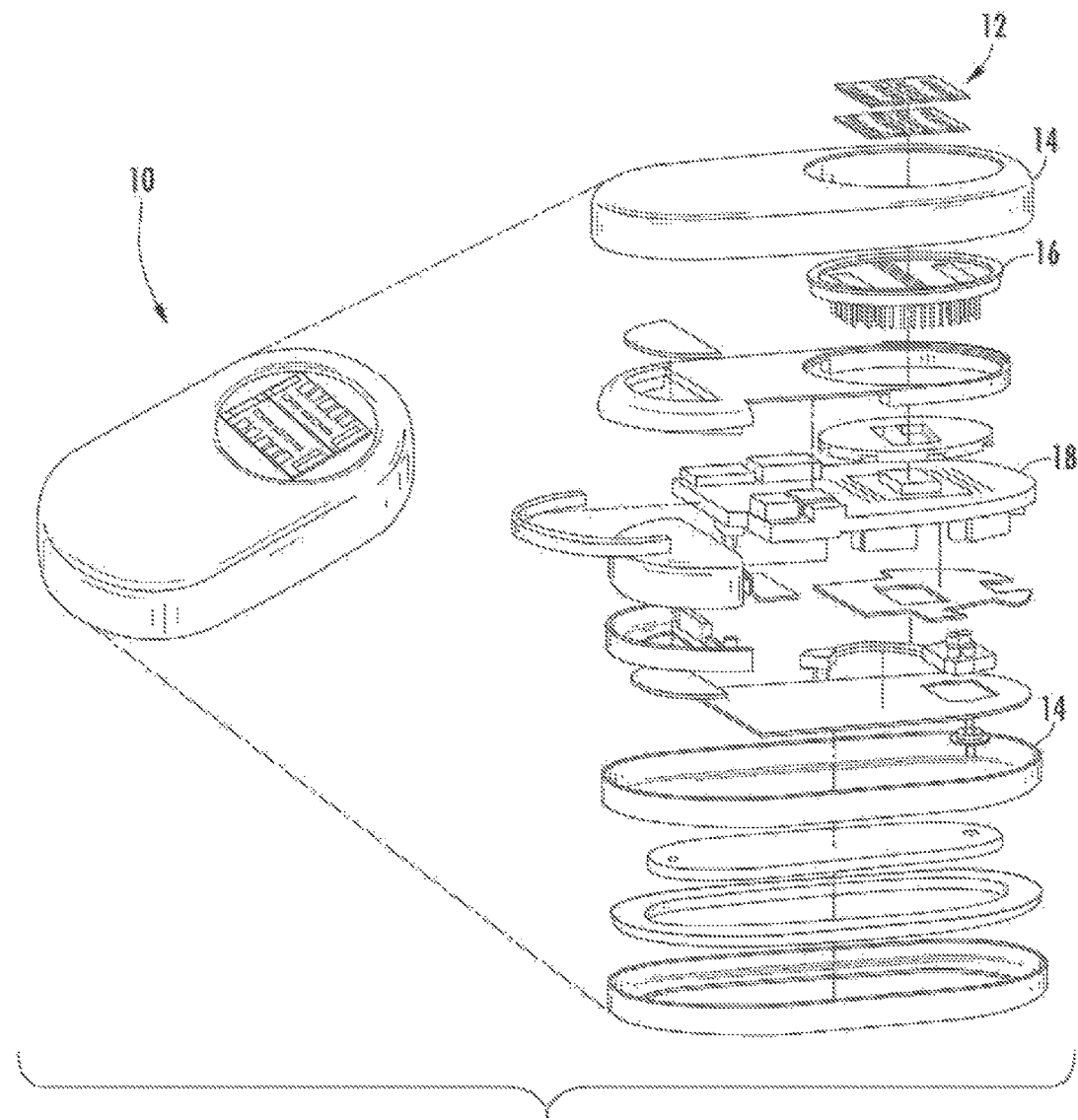
FIG. 1 schematically depicts an exploded perspective view of a prior art containment device including a microchip assembly.
Figure 2A:
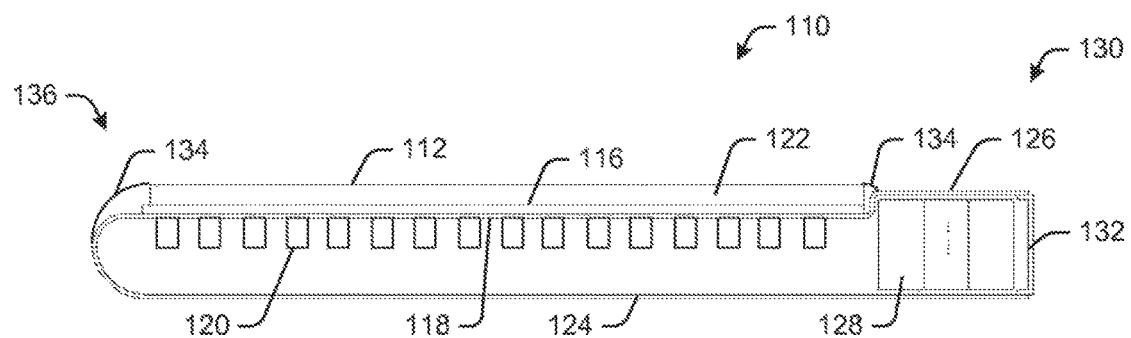
FIG. 2A schematically depicts a cross-sectional view of an assembled containment device including a microchip assembly according to an embodiment.
Figure 2B:
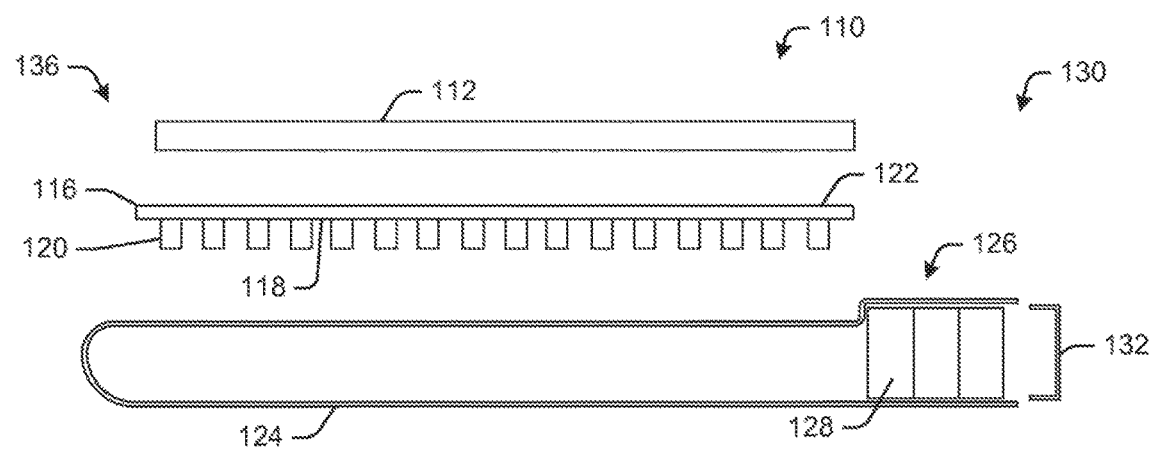
FIG. 2B schematically depicts an exploded cross-sectional view of the containment device shown in FIG. 2A.
Figure 2C:
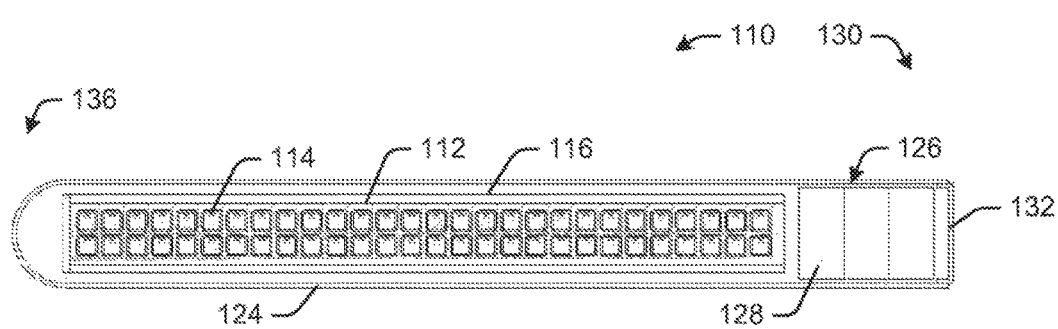
FIG. 2C schematically depicts a top view of the containment device shown in FIGS. 2A and 2B.
Figure 3:
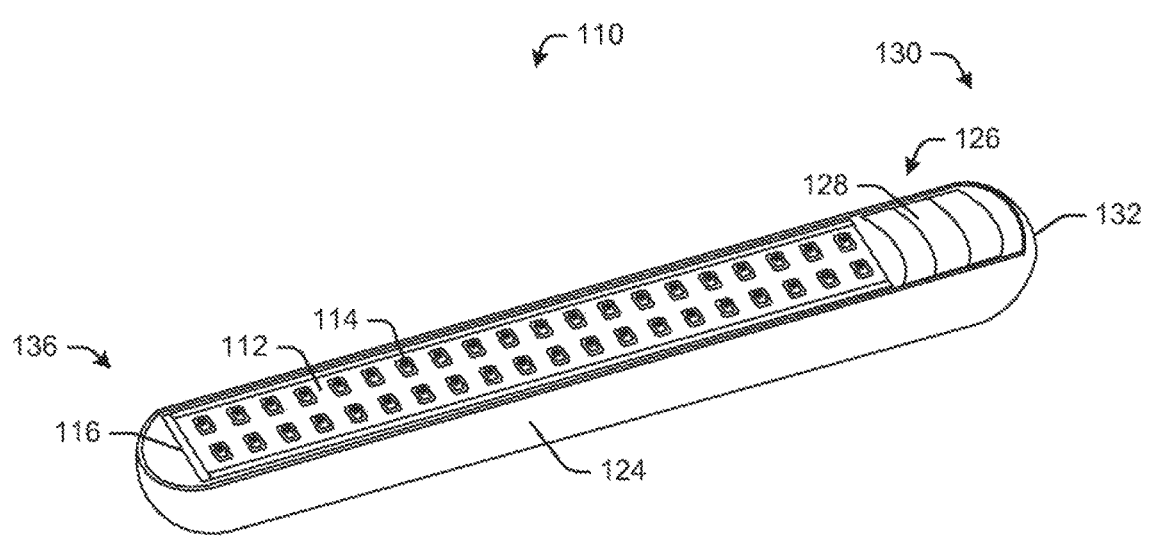
FIG. 3 schematically depicts a perspective view of the containment device illustrated in FIGS. 2A-2C.

The containment devices provided herein may be further understood with reference to the following exemplary embodiments, including the containment device 110 illustrated in FIGS. 2A-3. The containment device 110 includes an elongated microchip element 112 which comprises one or more containment reservoirs 114 that can be electrically activated to open. The containment device 110 also includes an elongated electronic printed circuit board (PCB) 116. The elongated PCB 116 comprises a biocompatible substrate and has a first side 118 on which one or more electronic components 120 are fixed and an opposed second side 122 on which the microchip element 112 is fixed in electrical connection to the one or more electronic components 120. As will be explained below with reference to FIG. 4, the electronic components 120 on the first side 118 of the PCB 116 are in electrical (i.e., operable) communication with the microchip element 112.

It is understood that the containment device 110 may include any suitable number of microchip elements 112 (e.g., from 1 to 6) and that each microchip element 112 may include a plurality of discrete containment reservoirs 114 (e.g., from 10 to 750 reservoirs). More microchip elements 112, and fewer or more containment reservoirs 114, per containment device 110 are also envisioned. Moreover, it is understood that the containment device 110 may include any suitable number of PCBs 116.

As shown in FIGS. 2A-2C, embodiments particularly suitable for minimally invasive insertion into a patient may have long, narrow microchip elements 112 with elongated arrays of closely spaced containment reservoirs. FIG. 2C shows a 2×28 reservoirs array. In one embodiment, the elongated array has from 1 to 4 rows of 20 to 40 reservoirs. In other embodiments, other numbers of rows and reservoirs are envisioned.

The "electronic printed circuit board" (PCB) refers to a substrate that mechanically supports and electrically connects electronic components using conductive pathways, tracks, or signal traces as known in the art. In certain embodiments, the PCB includes a biocompatible and hermetic substrate material. Suitable such materials include ceramics, such as alumina and silicon nitride. Multi-layer alumina PCBs have been successfully designed and manufactured. See, for example, U.S. Patent Application Publication No. 2003/0034564. These laminations may be the result of combining conductive layers, dielectric layers, and aluminum oxide ($Al_2O_3$, alumina) in a low temperature co-fired process. The alumina is referred to as low temperature co-fired ceramic (LTCC). These biocompatible ceramics also function as a hermetic barrier, eliminating the need, in some instances, for conventional metallic housing elements. Other materials or combinations of materials capable of performing all or some of the described function may also be used.

The term "biocompatible" as used herein generally refers to materials of construction that are suitable for long-term or short-term implantation into a human or animal subject, e.g., a patient. Such materials of constructions are known in the art of implantable medical devices.

As used herein, the term "hermetic seal" refers to preventing undesirable ingress or egress of chemicals (e.g., water vapor, water, oxygen, etc.) into or from one or more compartments of the device, such as the device reservoirs our housings, over the useful life of the device. For purposes herein, a material/seal that transmits helium (He) at a rate less than $1 \times 10^{-9}$ atm*cc/sec is termed hermetic.

In some instances, the containment device 110 may include an elongated housing 124. The elongated housing 124 is configured to hermetically seal the one or more electronic components 120 of the elongated PCB 116 within the elongated housing 124. That is, the elongated housing 124 is configured to surround the first side 118 of the elongated PCB 116. In this manner, the elongated housing 124 and the elongated PCB 116 collectively form a hermetic enclosure around the one or more electronic components 120. Desirably, the elongated housing 124 and at least a portion of the outward facing second side 122 of the elongated PCB 114 are formed of a biocompatible material. For example, in some instances, the elongated housing 124 may be made of a biocompatible metal or alloy, such as titanium or stainless steel. In other instances, the elongated housing 124 may be made of a biocompatible polymer. In certain embodiments, at least a portion of the elongated housing 124 may comprise a generally cylindrical body. Moreover, a distal end 136 of the elongated housing 124 may be rounded.

The elongated housing 124 may comprises a battery chamber 126 configured to house one or more batteries 128 therein. In some instances, the battery chamber 126 may be a separate area within the elongated housing 124. In other instances, the battery chamber 126 may be part of a single enclosure formed by the elongated housing 124. In one embodiment, the battery chamber 126 may be positioned about a proximal end 130 of the elongated housing 124. However, the battery chamber 126 may be located at any position within the elongated housing 124. Moreover, in some instances, the battery chamber 126 may be omitted. For example, the device power may be provided by inductive charging.

In certain embodiments, the battery chamber 126 may include a cover 132. The cover 132 may be removable or permanent. The cover 132 may be configured to provide access to the batteries 128 and/or hermetically seal the one or more batteries 128 within the battery chamber 126. That is, in a preferred embodiment, the cover 132 and the elongated housing 124 form a hermetic seal when affixed to each other. In one example, the cover 132 may be located about the proximal end 130 of the elongated housing 124.

The interface of the elongated housing 124 with the elongated PCB 116, in a preferred embodiment, forms a hermetic seal to isolate the one or more electronic components 120 within the elongated housing 124. In some instances, the elongated housing 124 may be welded to the elongated PCB 116. In other instances, a biocompatible substance 134, such as a biocompatible epoxy coating (e.g., an epoxy resin) or other biocompatible coating material, may be disposed over at least a portion of the elongated microchip element 112, the elongated PCB 116, and the elongated housing 124. This coating may be multilayered, and it may include a hermetic material so long the material does not interfere with the operation of any of the components, such as the electronic components 120 or the batteries 128.

In certain embodiments, the containment device 110 may include a sleek, tubular profile. For example, some or all of the components associated with the containment device 110 may be elongated. That is, some or all of the components of the containment device 110, such as the elongated microchip element 112, the elongated PCB 116, and the elongated housing 124, may have a greater length than width. Furthermore, the biocompatible coating substance 134, the elongated microchip element 112, and the elongated housing 124 may collectively form a generally circular cross-section and rounded distal end 136 of the containment device 110. The components may collectively fit together to form a sleek, tube-like structure or assembly that may be inserted in a human or animal subject in a minimally invasive manner. In other instances, some or all of the components associated with the containment device 110 may not be elongated.

The biocompatible coating substance 134 may create an atraumatic surface about the containment device 110. In embodiments, the surface of the containment device is formed of or coated with a lubricious substance to facilitate passage of the device to the intended tissue site.

The containment device 110 may be implanted in a human or animal subject, such as a patient in need of treatment, diagnosis, or prophylaxis, by a variety of techniques known in the art. In a preferred embodiment, the device is inserted into the patient at a subcutaneous tissue site. A variety of insertion tools and systems may be used depending on the particular size of the implant and the particular site of implantation desired for a particular medical purpose. The containment device 110 may be inserted, injected, or otherwise placed into the human or animal subject via one or a combination of minimally invasive medical instruments, including a cannula, trocar, subcutaneous insert, or a gun-like injector device or assembly. In one embodiment, a small (few millimeter) incision is made in the patient's skin, and the containment device is passed through the incision and into the patient just under the skin using a long, narrow inserter tool that can grasp an end of the containment device in a linear low profile arrangement. The containment device would be released from the inserter tool, the end of the inserter tool would be removed from the incision, and then the incision would be closed, for example with one or a few stitches. In some instances, one or more suture loops may be provided with the housing 124 and/or the cap 132. The suture loops may be configured to anchor the containment device 110 in a subcutaneous space.

The electronic components 120 provide any of a number of functions for the containment device 110. Examples include, but are not limited to, a controller (e.g., microprocessor) and power source (e.g., a battery or capacitor) for electrically activating the reservoir 114 to cause it to become opened and/to communicate with a sensor, for example, located within the reservoir 114 or with another device remotely located from the containment device 110. Other electronic components may include, for example, telemetry hardware, capacitors, transistors, and diodes, as well as the control means for actuating the reservoir caps. The control means may include an input source, a microprocessor, a timer, a demultiplexer (or multiplexer). In an embodiment, the electronic components include components for wirelessly receiving energy for charging an on-board storage capacitor, which may further reduce the space requirements for the electronic components on-board the containment device. In some instances, the electronic components may include an antenna.

The containment reservoir 114 of the microchip element 112 may be configured to open/activate in a variety of ways, which may be known in the art. In one embodiment, the containment reservoir 114 is structured and configured to be electrically activated to open as described in U.S. Pat. Nos. 7,510,551 and 7,604,628, which are incorporated herein by reference.

Figure 4:
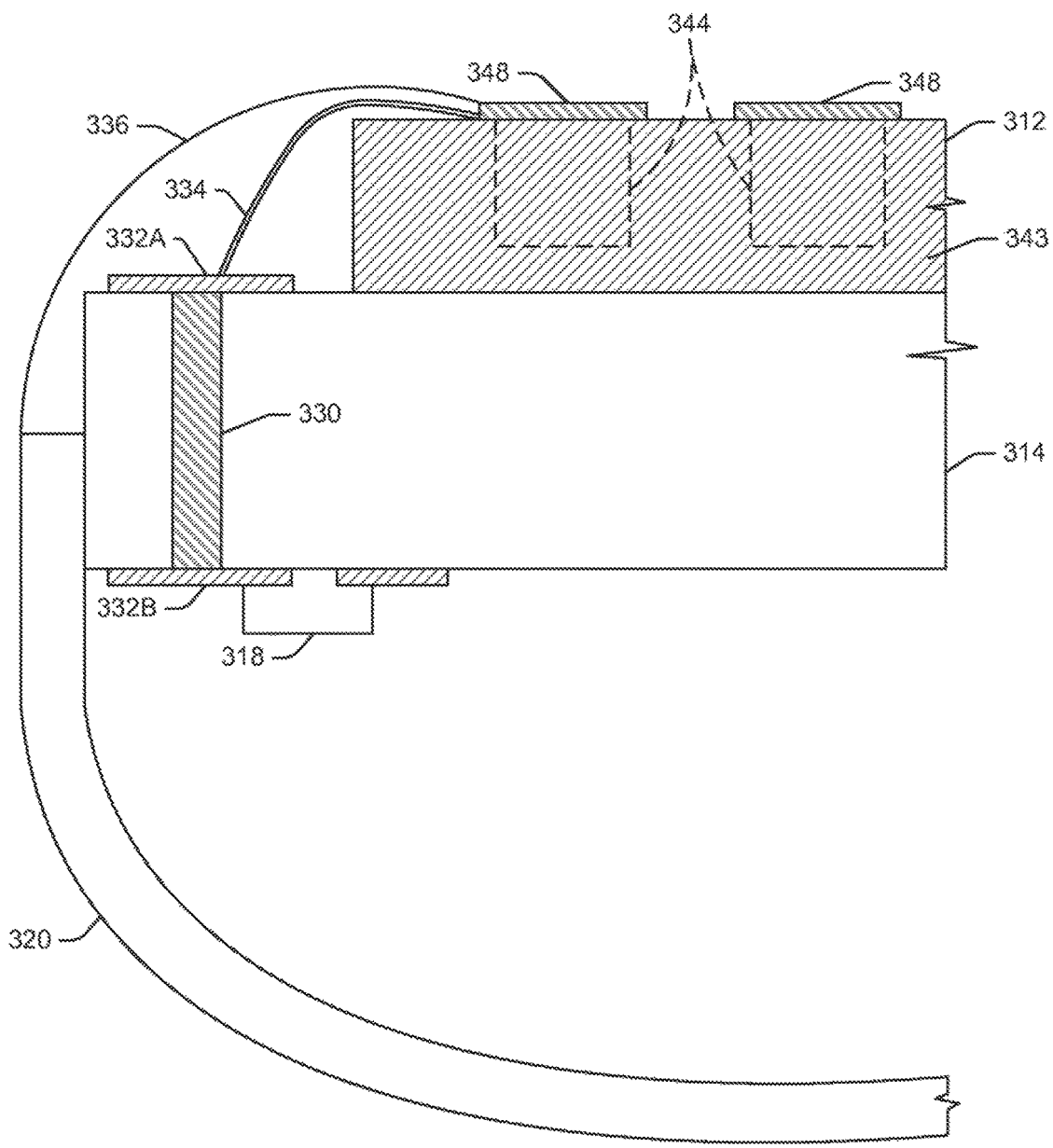
FIG. 4 schematically depicts a close-up, cross-sectional view of a portion of a containment device according to an embodiment.

One embodiment of the electrical connection between a PCB/electronic components and a microchip element is illustrated in FIG. 4. The figure shows part of the microchip element 312 including two containment reservoirs 344. Each containment reservoir 344 has an opening closed off by a reservoir cap 348. The containment reservoir 344, which is formed at least in part in a substrate 343, has a closed end opposed to the opening and a sidewall therebetween. The microchip element 312 is secured to a side of a PCB 314, and electronic component 318 is secured on the opposed side of the PCB 314. The PCB 314 includes a via 330 which electrically connects electronic component 318 to the microchip element 312. Via 330 is mechanically and electrically connected to metallized conductive surfaces 332A, 332B on the PCB 314, and the microchip element 312 is wirebonded 334 to the metallized conductive surface 332A. A biocompatible coating substance 336 is applied over the wire bond to secure and protect the connection, and typically will coat part of the surface of the PCB 314, part of the microchip element 312, and part of the housing 320 but not the reservoir caps 348. The coating substance 336 may be a polymer, such as an epoxy or other resin.

In one embodiment, the reservoir caps 348 are structured and configured to be electrically activated to open as described in U.S. Pat. Nos. 7,510,551 and 7,604,628, which are incorporated herein by reference. The reservoir caps 348 may be formed of a metal film, which may comprise a single layer or a laminate structure. For example, the reservoir cap 348 may comprise gold, platinum, titanium, or a combination thereof. In other embodiments, the reservoir cap 348 can be configured to be activated or opened by a mechanical or electrochemical mechanism.

The containment reservoir of the microchip element may be a "microreservoir" which generally refers to a reservoir having a volume equal to or less than 500 µL (e.g., less than 250 µL, less than 100 µL, less than 50 µL, less than 25 µL, less than 10 µL, etc.). In another embodiment, the containment reservoirs may be a "macroreservoir" which generally refers to a reservoir having a volume greater than 500 µL (e.g., greater than 600 µL, greater than 750 µL, greater than 900 µL, greater than 1 mL, etc.) and less than 5 mL (e.g., less than 4 mL, less than 3 mL, less than 2 mL, less than 1 mL, etc.). The terms "reservoir" and "containment reservoir" are intended to encompass both microreservoirs and macroreservoirs unless explicitly indicated to be limited to either one or the other.

In a second aspect, improved microchip elements and methods for their manufacture are provided. In a preferred embodiment, the microchip device element includes a relatively thin silicon substrate bonded to a relatively thicker primary substrate formed of a polymer or a glass or other ceramic material. Advantageously, by defining the reservoirs in the primary substrate rather than the silicon substrate, the reservoirs may be formed using processes other than dry reactive ion etching (DRIE). This is important, not just because DRIE processes are expensive, but also because under the conventional process, the DRIE processes occurred after deposition of the reservoir cap film, unnecessarily exposing the reservoir cap film to subsequent processing, which can negatively impact the yield of acceptable (e.g., hermetic) reservoir caps.

In addition, by adding the positive sealing features (e.g., gold sealing rings) to the silicon substrate, this keeps all of the high tolerance microfeatures to only the silicon substrate, which in turn frees up the primary substrate to be made by other, potentially lower tolerance, manufacturing processes. In this way, the reservoir can be made much deeper and thereby increase the unit reservoir payload. In one embodiment, the primary substrate is made by a casting or molding process using ceramic or polymeric materials that allows for formation of reservoirs that are deeper than conventional reservoirs and have smoother side walls than would be readily possible using DRIE. This cast or molded substrate then may be gold plated in and about sealing grooves formed therein for bonding with the positive sealing features on the silicon substrate.

Figure 5A:
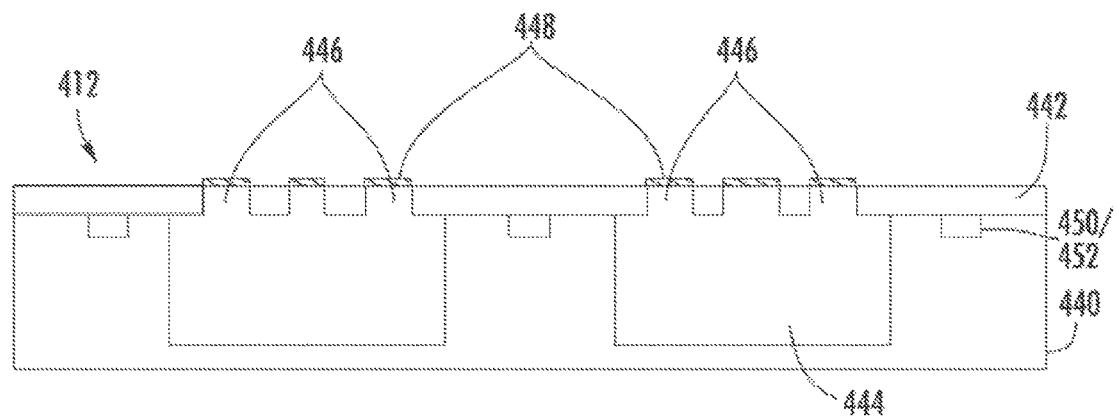
FIG. 5A schematically depicts a cross-sectional view of a microchip element assembly according to an embodiment.
Figure 5B:
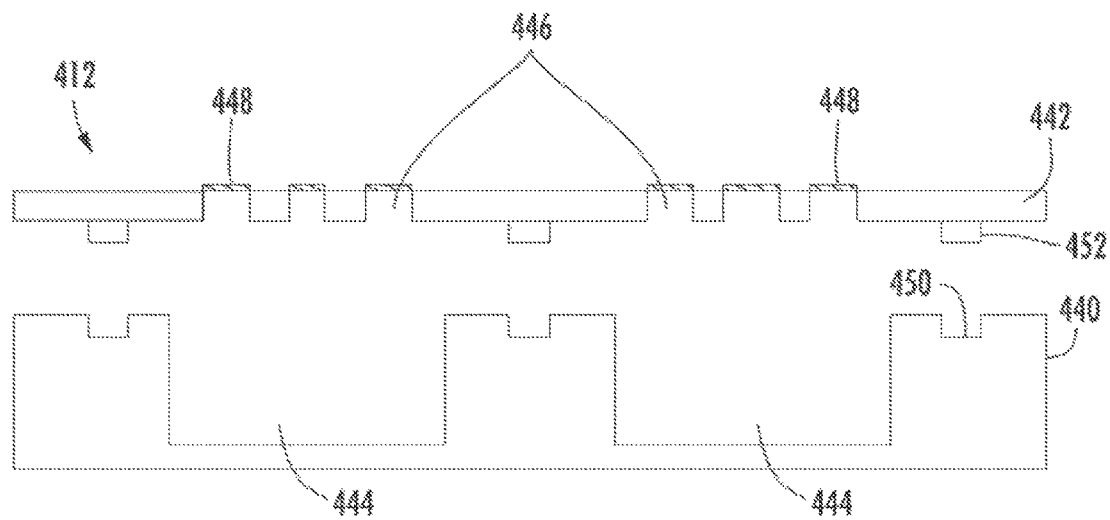
FIG. 5B schematically depicts an exploded cross-sectional view of the microchip element assembly shown in FIG. 5A.

An exemplary embodiment of the elongated microchip element is illustrated in FIG. 5A and FIG. 5B. The elongated microchip element 412 includes a primary substrate 440 and a silicon substrate 442, which are bonded together. The silicon substrate 442 has a first side, an opposed second side, and apertures 446 extending therethrough. Three apertures 446 are shown for each reservoir 444. The first side of the silicon substrate 442 includes reservoir caps 448 which close off the apertures until the reservoir needs to be opened. In a preferred embodiment, the reservoir caps 448 are electrically conductive. For example, the reservoir caps 448 may be in the form of a metal film. The silicon substrate 442, apertures 446, and reservoir caps 448 can be made using microfabrication techniques known in the art. For example, the photolithography, etching, and deposition techniques described in U.S. Pat. No. 7,604,628 may be used to form the apertures 446 in a polysilicon substrate closed off by metal reservoir caps 448.

The primary substrate 440 includes two reservoirs 444 in this illustration, although more or less reservoirs may be included. Each reservoir 444 is defined by a closed end wall, an open end, and at least one sidewall extending between the closed end wall and the open end. As mentioned above, the primary substrate 440 may be formed of silicon. In other embodiments, the substrate may be formed of a metaloid, polymer, glass, or other ceramic material. The substrate and reservoirs may be made by any suitable process, including but not limited to molding, casting, micromachining, and build-up or lamination techniques known in the art. In one embodiment, the primary substrate 440 is made of/by low temperature co-fired ceramics (LTCC). It may further include a coating layer on all or a portion of the substrate, for example to provide or improve hermeticity, biocompatibility, bonding, and/or reservoir content compatibility, stability, or release. Depending on the purpose of the coating layer, it may be applied inside the reservoirs 444, outside of the reservoirs 444, or both. Examples of possible coating materials include biocompatible metals, such as gold, and polymers, such as parylene.

The primary substrate 440 and the silicon substrate 442 are bonded together using any suitable method, to hermetically seal the reservoirs 444. In this way, the open end of the reservoir 444 is in fluid communication with the apertures 446 for controlled release or exposure of reservoir contents. In a preferred embodiment, the substrates are hermetically sealed together using a compression cold welding process, such as described in U.S. Pat. No. 8,191,756, which is incorporated herein by reference.

As shown in FIGS. 5A and 5B, the second side of the silicon substrate 442 includes ring structures 452 formed thereon, and the first side of the primary substrate 440 includes grooves 450. These bonding features are compressed together to form a cold weld bond hermetic seal surrounding the individual reservoirs 444. The ring structures 452 may be formed by a depositing gold or another metal layer on the silicon substrate 442. The grooves 450 may be etched in the silicon and then coated with a metallized layer of the same material as the metal ring. Variations of this embodiment are envisioned, for example, where other positive and negative bonding features are provided in/on either or both interfacing surfaces of the silicon substrate 442 and the primary substrate 440.

The primary substrate 440 is generally relatively thicker than the silicon substrate 442, and all or at least a majority (greater than 50%) of the reservoir sidewall height (or depth) is defined by the primary substrate 440. In an embodiment, the silicon substrate 442 has thickness that is between 5% and 50% of the thickness of the primary substrate 440 at the bonded interfaces of the substrates.

Although not shown in the FIG. 4 or FIG. 5A, the reservoirs 344 and 444, respectively, include reservoir contents positioned therewithin. The reservoirs can be configured to store essentially any substance or device component in need hermetic containment and subsequent release or exposure at a selected time. The reservoir content may be, for example, a chemical reagent, a drug formulation, or sensor or component thereof, such as an electrode. In an embodiment, a single device includes at least one containment reservoir containing a biosensor and at least one reservoir containing a drug formulation. Examples of various reservoir contents are described for example in U.S. Pat. Nos. 7,510,551; 7,497,855; 7,604,628; 7,488,316; and PCT WO 2012/027137.

Figure 6:
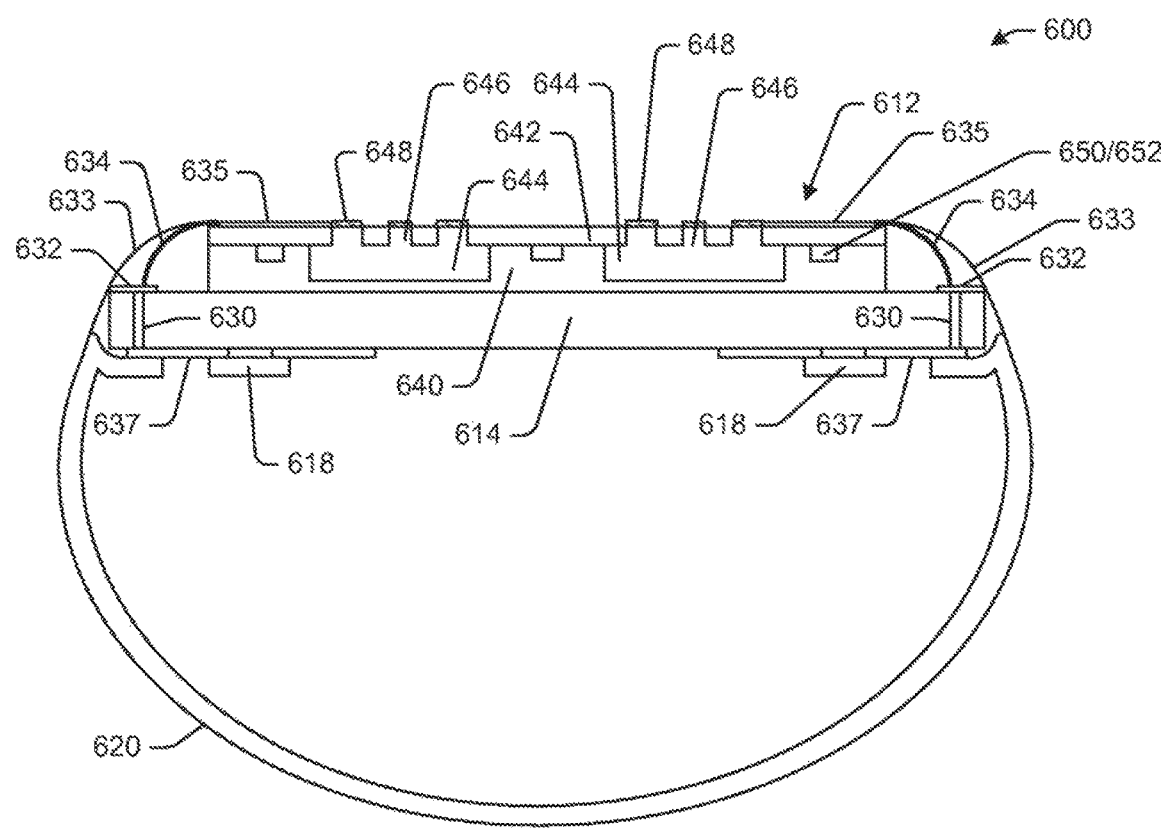
FIG. 6 schematically depicts a cross-sectional close-up view of a portion of an assembled containment device including a microchip assembly according to an embodiment.

An exemplary embodiment of a containment device 600 including a microchip element 612 is illustrated in FIG. 6. The containment device 600 includes a ceramic PCB 614 which has via 630 electrically connecting electronic component 618 to the microchip element 612. The electronic component 618 is secured on a first side of the ceramic PCB 614, and the microchip element 612 is secured on the opposing second side of the PCB 614. The via 630 electrically connects to a metallized conductive surface 632 on the first side of the PCB 614. The electrical circuitry 635 of the microchip element 612 is electrically connected to the metallized surface 632 by a wirebond 634. An epoxy 633 coats the wirebond 634 and at least a portion of the microchip element 612, the ceramic PCB 614, and a housing 620. In this manner, the epoxy 633 ensures that the containment device 600 is void of any atramatic surfaces. The second side of the ceramic PCB 614 also includes a metallized conductive surface 637, which is electrically connected to the electronic component 618. Although not shown in this illustration, the containment device 600 may include multiple microchip elements, as well as multiple vias, electronic components, and wirebonds. Moreover, the containment device 600 may be completely or partially coated by the epoxy 633.

The microchip element 612 includes a primary substrate 640 and a silicon substrate 642. The primary substrate 640 and silicon substrate 642 are bonded together by compression cold welding at/adjacent the interface of a ring structure and groove structure tongue 650/652. Reservoirs 644 are defined in the primary substrate 640 with the open end in fluid communication with apertures 646 defined through the silicon substrate 612. Electrically conductive reservoir caps 648 sealingly cover the apertures 646 and reservoirs 644.

Figure 7:
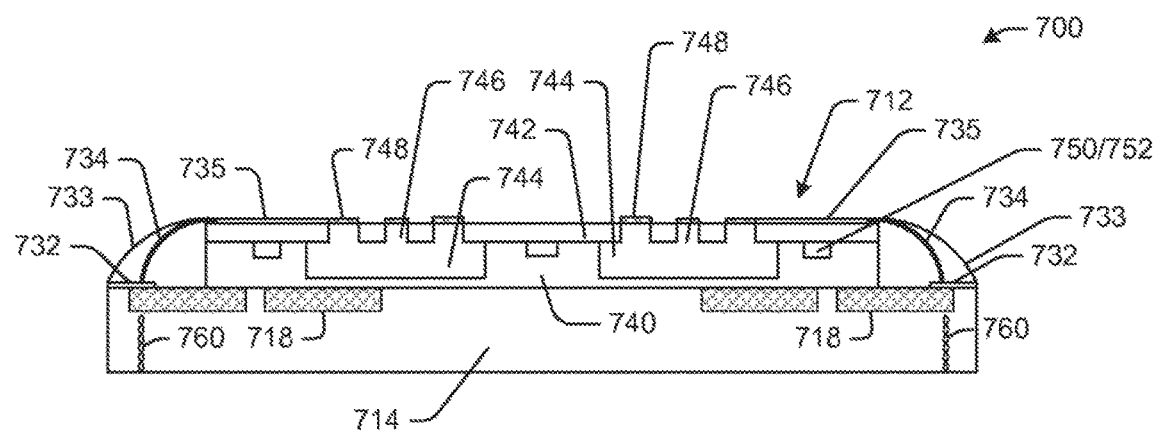
FIG. 7 schematically depicts a cross-sectional close-up view of a portion of an assembled containment device including a microchip assembly according to an embodiment.

An exemplary embodiment of a containment device 700 is illustrated in FIG. 7. The containment device 700 includes a microchip element 712 and a ceramic PCB 714, which is fixed to the microchip element 712. Electrical circuitry 735 of the microchip element 712 is electrically connected to the metallized surface 732 by a wirebond 734. An epoxy 733 coats the wirebond 734 and at least a portion of the microchip element 712, the ceramic PCB 714, and/or the metallized surface 732. In this manner, the epoxy 733 ensures that the containment device 700 is void of any atramatic surfaces. Although not shown in this illustration, the containment device 700 may include multiple microchip elements, as well as multiple vias, electronic components, and wirebonds. Moreover, the containment device 700 may be completely or partially coated by the epoxy 733. In some instances, the containment device 700 may be relatively thin and the epoxy coating may be omitted. The containment device 700 may include any length, to width, to thickness ratio. That is, the containment device 700 may be any suitable size.

In some instances, the PCB 714 may comprise a silicon material that is manufactured using a MEMS manufacturing process. In other instances, the PCB 714 may comprise a multilayer low temperature co-fired ceramic (LTCC). In yet other instances, the PCB 714 may comprise a substrate other than a printed circuit board that is capable of performing the functionality described herein. For example, element 714 may comprise a silicon substrate or the like that is configured to house one or more electric components 718 therein. In turn, the electrical components 718 may be in communication with the microchip element 712.

The microchip element 712 includes a primary substrate 740 and a silicon substrate 742. The primary substrate 740 and silicon substrate 742 are bonded together by compression cold welding at/adjacent the interface of a ring structure and groove structure tongue 750/752. The reservoirs 744 are defined in the primary substrate 740 with the open end in fluid communication with the apertures 746 defined through the silicon substrate 742. Electrically conductive reservoir caps 748 sealingly cover the apertures 746 and reservoirs 744. In some instances, the PCB 714 and the primary substrate 740 may comprise a single silicon substrate or separate silicon substrates. In this manner, the PCB 714 and the primary substrate 740 may be manufactured together as part of a MEMS process or manufactured separately and assembled together.

In certain embodiments, in order to provide a smaller and less intrusive containment device 700, the housing is omitted. In this manner, the electronic components 718 are integrated into the microchip element 712 and/or the ceramic PCB 714. That is, the electronic components 718 may be disposed within or about the microchip element 712 and/or the ceramic PCB 714. In some instances, the electronic components 718 include components and/or functionality for wirelessly receiving energy for charging an on-board storage capacitor, which may further reduce the space requirements for the electronic components on-board the containment device 700. In some instances, the electronic components 718 may include an antenna or the like. In addition, an inductive coupling device 760, such as a coil or the like, may be incorporated into the microchip element 712 and/or the ceramic PCB 714. In certain embodiments, the electronic components 718 and the inductive coupling device 760 may be integrated. In other embodiments, the electronic components 718 and the inductive coupling device 760 may be separate components in electrical (i.e., operable) communication with one another. The inductive coupling device 760 may form an inductive coupling circuit between the implanted containment device 700 and an external communicator, such as a power source and/or computing device or the like. The electronic components 718 and/or the inductive coupling device 760 provide, for example, functionality to receive wireless power transmission from the external communicator, capacitors to store the required energy to open the caps 748, and/or other electronics and circuitry to manage the flow of current to the appropriate reservoirs 744. Other functionality also may be provided by the electronic components 718 and/or the inductive coupling device 760.

Figure 8:
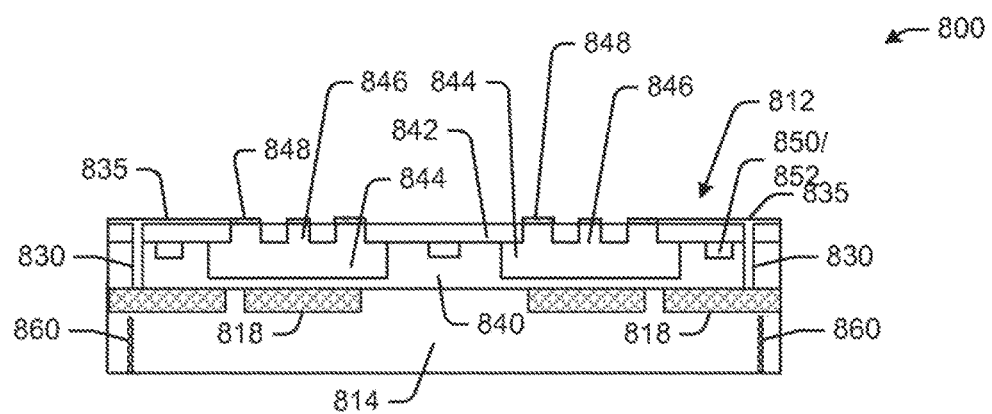
FIG. 8 schematically depicts a cross-sectional close-up view of a portion of an assembled containment device including a microchip assembly according to an embodiment.

An exemplary embodiment of a containment device 800 is illustrated in FIG. 8. The containment device 800 includes a microchip element 812 and a ceramic PCB 814, similar to those described above. That is, the ceramic PCB 814 is fixed to the microchip element 812. A via 830 electrically connects electronic components 818 to portions of the microchip element 812. For example, the electrical circuitry 835 of the microchip element 812 is electrically connected to the electronic components 818 by way of the via 830. Although not shown in this illustration, the containment device 800 may include multiple microchip elements, as well as multiple vias, electronic components, wirebonds, and/or epoxy coatings that ensure the containment device 800 is void of any atramatic surfaces (i.e., the containment device 800 may be completely or partially coated by an epoxy). In some instances, the containment device is relatively thin and the epoxy coating may be omitted. The containment device 800 may include any length, to width, to thickness ratio. That is, the containment device 800 may be any suitable size.

In certain embodiments, the PCB 814 may comprise a silicon material that is manufactured using a MEMS manufacturing process. In other instances, the PCB 814 may include a multilayer low temperature co-fired ceramic (LTCC). In yet other instances, the PCB 814 may include a substrate other than a printed circuit board that is capable of performing the functionality described herein. For example, element 814 may include a silicon substrate or the like that is configured to house one or more electric components 818 therein. In turn, the electrical components 818 may be in communication with the microchip element 812.

The microchip element 812 includes a primary substrate 840 and a silicon substrate 842. The primary substrate 840 and silicon substrate 842 are bonded together by compression cold welding at/adjacent the interface of a ring structure and groove structure tongue 850/852. The reservoirs 844 are defined in the primary substrate 840 with the open end in fluid communication with the apertures 846 defined through the silicon substrate 842. Electrically conductive reservoir caps 848 sealingly cover the apertures 846 and reservoirs 844. In some instances, the PCB 814 and the primary substrate 840 may comprise a single silicon substrate or separate silicon substrates. In this manner, the PCB 814 and the primary substrate 840 may be manufactured together as part of a MEMS process or manufactured separately and assembled together.

Similar to the embodiments described in FIG. 7, in order to provide a smaller and less intrusive containment device 800, the housing is omitted. As a result, the electronic components 818 are integrated into the microchip element 812 and/or the ceramic PCB 814. That is, the electronic components 818 may be disposed within or about the microchip element 812 and/or the ceramic PCB 814. In some instances, the electronic components 818 include components and/or functionality for wirelessly receiving energy for charging an on-board storage capacitor, which may further reduce the space requirements for the electronic components on-board the containment device 800. In some instances, the electronic components 818 may include an antenna or the like. In addition, an inductive coupling device 860, such as a coil or the like, may be incorporated into the microchip element 812 and/or the ceramic PCB 814. In certain embodiments, the electronic components 818 and the inductive coupling device 860 may be integrated. In other embodiments, the electronic components 818 and the inductive coupling device 860 may be separate components in electrical (i.e., operable) communication with one another. The inductive coupling device 860 may form an inductive coupling circuit between the implanted containment device 800 and an external communicator, such as a power source and/or computing device or the like. The electronic components 818 and/or the inductive coupling device 860 provide, for example, functionality to receive wireless power transmission from the external communicator, capacitors to store the required energy to open the caps 848, and/or other electronics and circuitry to manage the flow of current to the appropriate reservoirs 844. Other functionality also may be provided by the electronic components 818 and/or the inductive coupling device 860.

Figure 9:
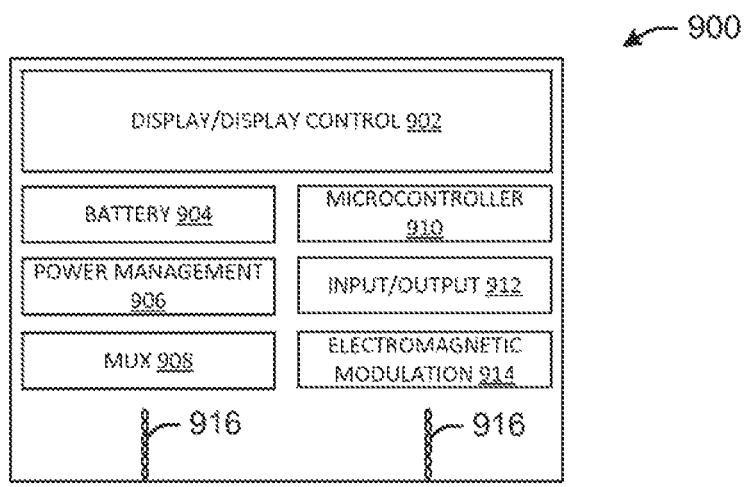
FIG. 9 schematically depicts an external communicator that may be configured to wirelessly communicate with a containment device according to an embodiment.

An exemplary embodiment of an external communicator 900 (or controller) is illustrated in FIG. 9. In certain embodiments, the external communicator 900 includes a display 902, a battery 904 (or other power supply), a power management module 906, a multiplexer 908, a microcontroller 910, an input/output module 912, and/or an electromagnetic modulation module 914. In addition, the external communicator 900 includes one or more processors coupled to at least one memory. In this manner, various instructions, methods, and techniques described herein may be considered in the general context of computer-executable instructions, such as program modules, executed by one or more computers or other devices. Additional components and/or modules may be included. Moreover, the external communicator 900 includes an inductive coupling device 916. The inductive coupling device 916 forms an inductive coupling circuit between the implanted containment device and the external communicator 900 when brought within proximity of one another.

In some instances, the external communicator 900 may be a hand held device. In other instances, the external communicator 900 may be associated with a computer or the like. In yet other instances, the external communicator 900 may be wireless. The external communicator 900 may include any number of interfaces so that a user may interact therewith. Moreover, the external communicator 900 may include any number of interfaces and/or functionality so that the external communicator 900 may wirelessly interact with a containment device.

Figure 10:
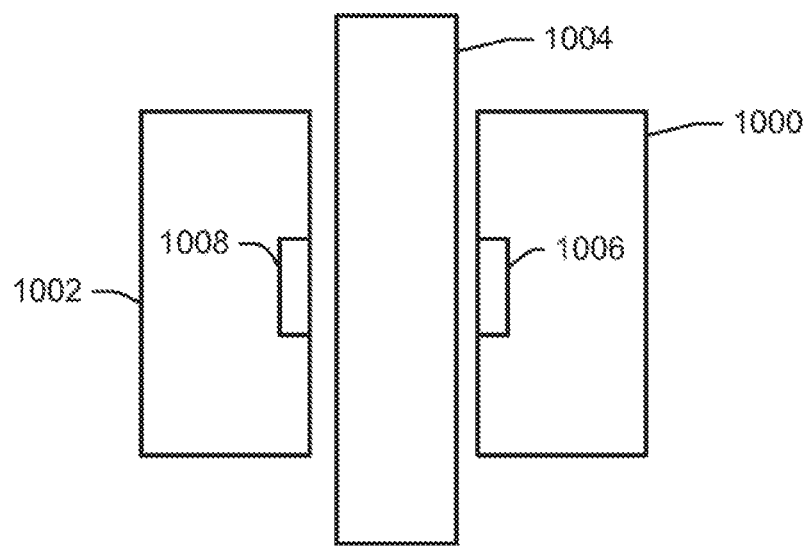
FIG. 10 schematically depicts an external communicator positioned adjacent to an implanted containment device according to an embodiment.

As depicted in FIG. 10, in some instances, an external communicator 1000 may be positioned on or about the surface of the skin 1004 adjacent to a containment device 1002 that is implanted within a patient. For example, in one embodiment the site of implantation is subcutaneous and near to the skin of the patient. The external communicator 1000 includes an inductive coupling device 1006 or the like, and the containment device 1002 includes an inductive coupling device 1008 or the like. In this manner, the external communicator 1000 may be configured to transmit both control instructions and the necessary power to release the required dose or doses by way of an inductive coupling between the inductive coupling device 1006 and the inductive coupling device 1008. In certain embodiments, the external communicator 1000 may query the implanted containment device 1002 to obtain diagnostic information or confirmation information, such as specific doses released and doses remaining.

The use of the external communicator 1000 advantageously significantly reduces the overall size of the containment device 1002 by relocating the power source and several of the control functions from the containment device 1002 to the external communicator 1000. For example, both power and control signals can be transferred across the skin 1004 via electromagnetic coupling, such as inductive charging or the like. Other wireless communications and connections may also be incorporated between the external communicator 1000 and the containment device 1002. In this manner, the external communicator 1000 may control one or more aspects of the containment device 1002 remotely.

The reduction in the size (i.e., volume) of the containment device 1002 beneficially leads to reductions in the incision required to implant the containment device 1002 under the skin 1004. The reduction in the size of the containment device 1002 also beneficially increases the possible locations in the body that the containment device 1002 can be implanted, which may be important for local or regional delivery of therapeutic agents and/or may reduce the amount of drug required to be delivered for a particular therapy. Moreover, the reduction in the size of the containment device 1002 makes the containment device 1002 less intrusive for the patient. As a result, the containment device 1002 may comprise a drug delivery implant with a higher ratio of drug volume to total device volume.

Modifications and variations of the methods and devices described herein will be obvious to those skilled in the art from the foregoing detailed description. Such modifications and variations are intended to come within the scope of the appended claims.

I claim:

1. An implantable medical device, comprising:
   a microchip element which comprises
      reservoirs that are configured to be electrically activated to open, the reservoirs each containing a drug formulation or a sensor element;
      a silicon substrate having a first side, an opposed second side, and at least one aperture extending therethrough, wherein the first side of the silicon substrate comprises an electrically conductive reservoir cap which closes off the at least one aperture; and
      a primary substrate which is formed of silicon or other metalloid, a polymer, or a glass or other ceramic material, wherein the second side of the silicon substrate is hermetically bonded to the primary substrate and wherein the reservoirs containing the drug formulation or the sensor element are defined therebetween, an open end of each reservoir being in fluid communication with the at least one aperture for controlled release of the drug formulation or controlled exposure of the sensor element;
   an electronic printed circuit board (PCB) fixed to the microchip element, the PCB comprising a biocompatible substrate, which is alumina or another ceramic;
   one or more electronic components associated with the microchip element or the PCB; and
   a first inductive coupling device incorporated into the microchip element, wherein the first inductive coupling device is in communication with the one or more electronic components,
   wherein the implantable medical device does not include a header or feedthrough.

2. The device of claim 1, wherein the PCB comprises at least one via configured to electrically connect at least one of the one or more electronic components to the microchip element.

3. The device of claim 1, wherein the microchip element is wirebonded via a wire bond to a metallized conductive surface on the PCB.

4. The device of claim 3, wherein a biocompatible coating substance is positioned over the wire bond to secure and protect a connection formed by the wire bond.

5. The device of claim 1, wherein the primary substrate comprises a metal coating over at least a part of the polymer, glass or other ceramic material of the primary substrate.

6. The device of claim 5, wherein the metal coating coats a sidewall and/or a closed end wall of each of the reservoirs.

7. The device of claim 1, wherein the second side of the silicon substrate comprises at least one metal ring structure formed thereon.

8. The device of claim 7, wherein the at least one ring structure comprises gold.

9. The device of claim 8, wherein the primary substrate comprises at least one groove structure, wherein the at least one ring structure and the at least one groove structure together form a hermetic bond.

10. The device of claim 1, wherein the reservoirs contain a drug formulation, a total amount of the drug formulation in the device being a drug payload.

11. The device of claim 10, wherein a ratio of a volume of the drug payload to a total volume of the device is from about 75 µL/cc to about 150 µL/cc.

12. The device of claim 11, wherein the ratio of the volume of the drug payload to the total volume of the device is from about 85 µL/cc to about 120 µL/cc.

13. A system comprising:
   the implantable medical device of claim 1, which is configured for implantation in a patient; and
   an external communicator comprising a second inductive coupling device configured to form an inductive coupling circuit with the first inductive coupling device when brought within proximity of the implantable medical device.

* * * * *